United States Patent
Gray

(10) Patent No.: US 6,276,363 B1
(45) Date of Patent: *Aug. 21, 2001

(54) PORTABLE EMERGENCY SAFETY RESUSCITATOR

(76) Inventor: David Scott Gray, 147 Spanish Moss Pl., Camarillo, CA (US) 93010

(*) Notice: Subject to any disclaimer, the term of this patent is extended or adjusted under 35 U.S.C. 154(b) by 0 days.

This patent is subject to a terminal disclaimer.

(21) Appl. No.: 09/570,154

(22) Filed: May 12, 2000

Related U.S. Application Data

(63) Continuation of application No. 09/193,424, filed on Nov. 17, 1998, now Pat. No. 6,062,217.

(51) Int. Cl.[7] .............................. A61M 16/00; A62B 7/10
(52) U.S. Cl. .............................. 128/205.13; 128/205.17; 128/205.23; 128/205.24; 128/203.28; 128/202.27
(58) Field of Search ........................ 128/205.13, 205.17, 128/205.23, 205.24, 203.28, 202.27

(56) References Cited

U.S. PATENT DOCUMENTS

| | | | |
|---|---|---|---|
| 3,650,093 | * | 3/1972 | Rosenberg .............................. 55/159 |
| 5,279,289 | * | 1/1994 | Kirk ................................. 128/205.23 |
| 5,749,358 | * | 5/1998 | Good et al. ...................... 128/205.23 |
| 6,062,217 | * | 5/2000 | Gray ................................. 128/205.13 |

* cited by examiner

*Primary Examiner*—John G. Weiss
*Assistant Examiner*—Mital B. Patel
(74) *Attorney, Agent, or Firm*—Thompson E. Fehr

(57) ABSTRACT

A resuscitator having a collapsible bag with an inlet for attachment to a source of oxygen. The collapsible bag has a major outlet and a minor outlet. The major outlet is connected to a first arm of a three-armed connector. The minor outlet is attached to a flexible tube which, in turn, may either be connected to an adapter that is connected to the second arm of the three-armed connector or to a nebulizer or aerosolizer that is attached to the second arm of the three-armed connector. The third arm of the three-armed connector is connected to a housing containing a one-way valve to permit the flow of oxygen away from the collapsible bag and to preclude the flow of liquids and gases toward the collapsible bag. Preferably, the housing also contains, between the one-way valve and the second end of the housing, an exhaust aperture; and the exhaust aperture is preferably covered by a filter. The second end of the housing is attached to the first aperture of a tube that has a self-sealing membrane removably covering a second aperture and a third aperture that may be connected either to a mask or an endotracheal tube. And a carbon dioxide detector may optionally be inserted into the exhaust aperture.

11 Claims, 3 Drawing Sheets

PORTABLE EMERGENCY SAFETY RESUSCITATOR

CROSS-REFERENCE TO RELATED APPLICATION

This is a continuation of copending U.S. application Ser. No. 09/193,424, filed on 11/17/98, which will issue as U.S. Pat. No. 6,062,217.

BACKGROUND OF THE INVENTION

1. Field of the Invention

This invention relates to a medical device and more particularly to a resuscitator, i.e., a manually operated device utilized to provide emergency ventilatory assistance to facilitate the breathing of a sick or injured patient.

2. Description of the Related Art

The inventor is unaware of any prior art resuscitator which incorporates the ability to provide endotracheally administered medications, nebulized medications, and suction to a patient.

U.S. Pat. No. 5,575,279 of Douglas K. Beplate describes an isolation valve to be used by a care giver who is blowing such care giver's own breath into the lungs of a patient. The isolation valve of that patent employs a check valve to force the breath of the patient through an exhalation filter before such breath can reach the surrounding environment.

SUMMARY OF THE INVENTION

The present invention inserts, between a source of air or oxygen and a patient, a collapsible bag and a connecting complex. A nebulizer or aerosolizer for providing medication can be attached to the connecting complex. Additionally, the connecting complex includes an aperture with a removably attached self-sealing membrane through which medications can be administered with a syringe. When the self-sealing membrane has been removed, a suction catheter may be placed through the aperture.

The connecting complex can communicate with the patient either through a mask or an endotracheal tube.

A one-way valve precludes liquids or gases expelled by the patient from reaching either the point of attachment for the nebulizer and aerosolizer or the collapsible bag.

A filtered exhaust aperture permits the exhaled breath of the patient to reach the atmosphere. A carbon dioxide detector placed in the exhaust aperture indicates whether the patient is breathing.

And utilizing a filter that has both a hydrophobic segment and a hydrophilic segment minimizes that chances that a harmful microorganism that associates with liquids will enter the surrounding environment.

DESCRIPTION OF THE PREFERRED EMBODIMENT

Figure 1:
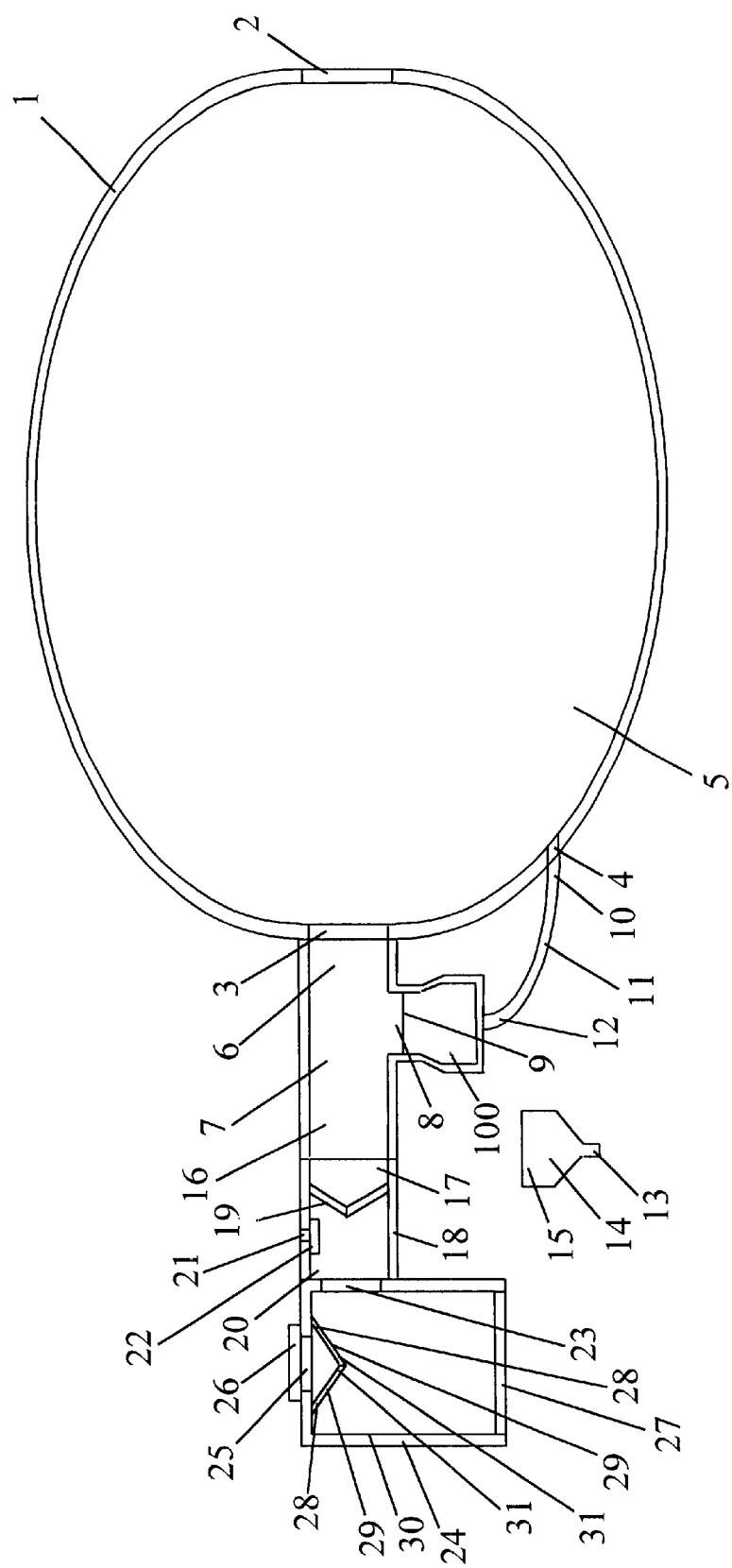
FIG. 1 illustrates the Portable Emergency Safety Resuscitator.

The present invention utilizes a collapsible bag 1 having an inlet 2, a major outlet 3, and a minor outlet 4. Attached to the major outlet 3 of the collapsible bag 1 and communicating with the interior 5 of the collapsible bag 1 is a first arm 6 of a hollow three-armed connector 7.

A second arm 8 of the hollow three-armed connector 7 is available for attachment to a nebulizer or aerosolizer 100. The open end 9 of the second arm 8 is preferably sized to accommodate commercially available nebulizers and aerosolizers 100.

A first end 10 of a flexible tube 11 is attached to the minor outlet 4 of the collapsible bag 1. A second end 12 of the flexible tube 11 may be attached to a nebulizer or aerosolizer 100. If no nebulizer or aerosolizer 100 is employed, the second end 12 of the flexible tube 11 is attached to the open end 9 of the second arm 8 of the hollow three-armed connector 7.

The inlet 2 of the collapsible bag 1 is available to be releasably connected to a source of air or, preferably, oxygen. When such connection has been made, oxygen can flow into the interior 5 of the collapsible bag 1, through the collapsible bag 1, through the major outlet 3 of the collapsible bag 1, and into the first arm 6 of the hollow three-armed connector 7.

Oxygen can also flow through the minor outlet 4 of the collapsible bag 1 and through the flexible tube 11. If the flexible tube 11 has been connected to a nebulizer or aerosolizer 100, the oxygen will then enter the nebulizer or aerosolizer 100 and carry medication from such nebulizer or aerosolizer 100 into the second arm 8 of the hollow three-armed connector 7. If no nebulizer or aerosolizer 100 has been attached to the open end 9 of the second arm 8 of the hollow three-armed connector 7, the flexible tube 11 is attached to a first end 13 of a hollow adapter 14; and a second end 15 of the hollow adapter 14 is connected to the second arm 8 of the hollow three-armed connector 7. Oxygen can then flow from the flexible tube 11, through the hollow adapter 14, and into the second arm 8 of the hollow three-armed connector 7.

Preferably, the major outlet 3 and the minor outlet 4 are of such sizes that the flow of oxygen through the major outlet 3 is 17 liters per minute; and the flow of oxygen through the minor outlet 4 is 8 liters per minute when the collapsible bag 1 is receiving oxygen at a typical rate of flow from a source of oxygen. Also, the collapsible bag 1 may be squeezed by a care giver to vary the rate of flow of oxygen.

Attached to and communicating with a third arm 16 of the hollow three-armed connector 7 is a first end 17 of a housing 18 containing one-way valve 19 to permit air, oxygen, and medication to flow toward the patient but to preclude the transmission of liquids or gases flowing from the patient.

Preferably, the housing 18 also contains, between the one-way valve 19 and the second end 20 of the housing 18, an exhaust aperture 21 through which the exhaled breath of the patient can reach the atmosphere. Also preferably, a filter 22 covers the exhaust aperture 21 to minimize the possibility that contaminants from the patient will enter the atmosphere.

And the hollow three-armed connector 7 is preferably T-shaped.

Attached to and communicating with a second end 20 of the housing 18 is a first aperture 23 of a tube 24. The tube 24 is preferably L-shaped. And the hollow three-armed connector 7, the housing 18, and the tube 24 are preferably constructed of rigid clear plastic.

A second aperture 25 of the tube 24 is releasably covered by a self-sealing membrane 26. The self-sealing membrane is preferably siliconized.

To a third aperture 27 of the tube 24 may be connected either a mask or an endotracheal tube.

When the endotracheal tube is employed, the needle of a syringe can be inserted through the self-sealing membrane 26, through the second aperture 25, through the tube 24, through the third aperture 27, and into the endotracheal tube so that medications can be pushed from the syringe into the endotracheal tube for the patient.

Alternatively, when the self-sealing membrane 26 has been removed from the second aperture 25 of the tube 24, a suction catheter may be inserted through the second aperture 25, through the tube 24, through the third aperture 27, and through the endotracheal tube to remove fluids such as blood, emesis, and secretions from the patient's airway in order to permit the patient to breathe.

Preferably, first ends 28 of strips of flexible plastic 29 are attached to the inside 30 of the tube 24 between the first aperture 23 and the second aperture 25. The second ends 31 of the strips of flexible plastic 29 push against one another so that when a suction catheter is inserted, a seal is formed between the inside 30 of the tube 24 and the suction catheter to preclude contamination from the patient escaping into the atmosphere. The location of the strips of flexible plastic 29 prevents their interfering with the flow of oxygen from the first aperture 23 to the third aperture 27.

Figure 2:
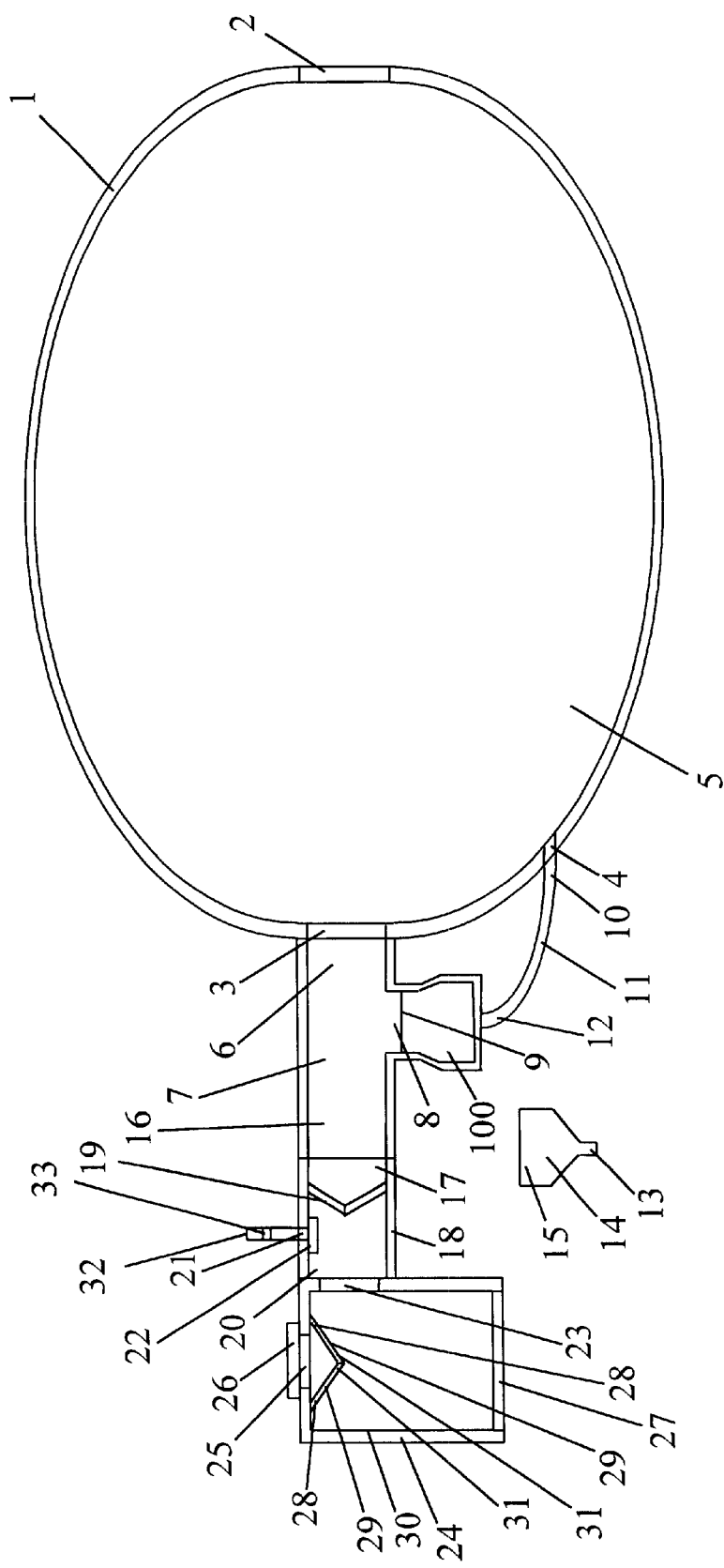
FIG. 2 shows a carbon dioxide detector attached to the exhaust aperture of the Portable Emergency Safety Resuscitator.

Optionally, as illustrated in FIG. 2, a carbon dioxide detector 32 is inserted into the exhaust aperture 21. The carbon dioxide detector 32, of course, indicates, in any manner that is well known in the art, the presence of carbon dioxide, which shows that the patient is breathing.

The carbon dioxide detector 32 is so constructed as not significantly to impair the flow of the exhaled air and can optionally contain its own filter, which, for clarity, is designated the detector filter 33.

Figure 3:
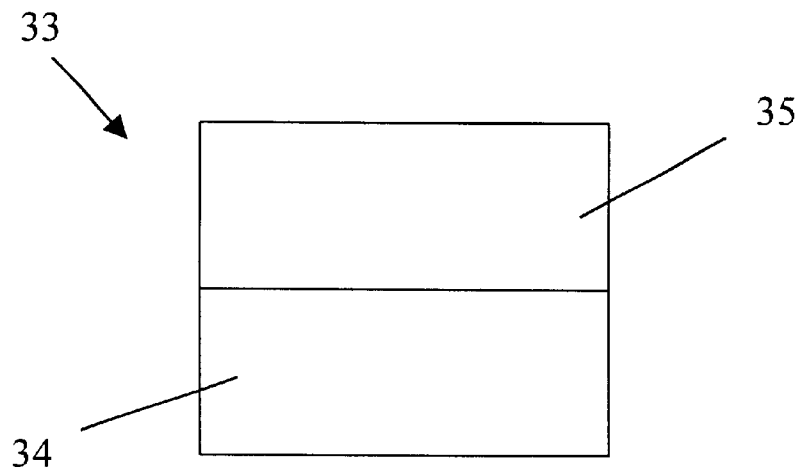
FIG. 3 depicts a filter having a hydrophobic segment and a hydrophilic segment that are adjacent to one another.
Figure 4:
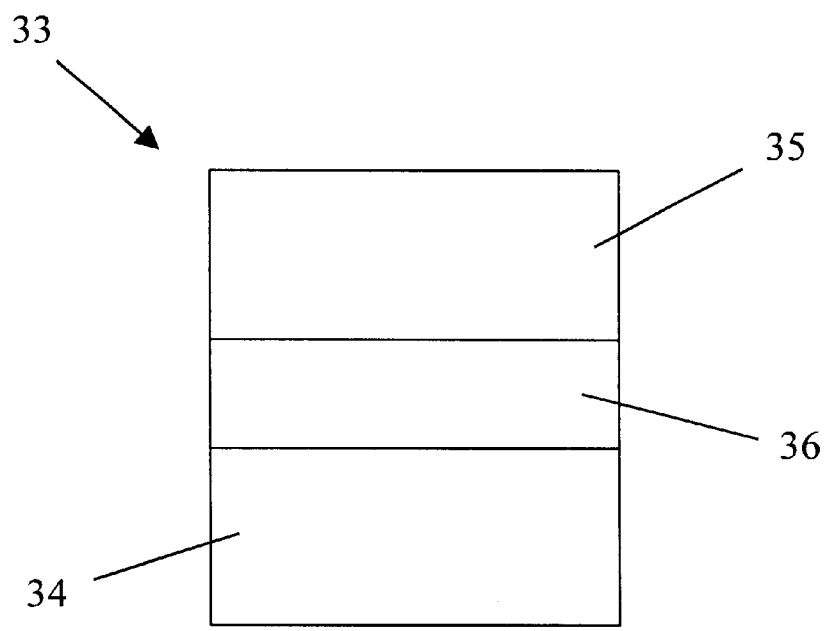
FIG. 4 portrays a filter having a hydrophobic segment and a hydrophilic segment spaced apart from one another.

Preferably, the filter 22 and the detector filter 33 consist, as shown in FIG. 3, of a first segment 34 that is hydrophobic and a second segment 35 that is hydrophilic in order to retard the passage of moisture, which frequently contains harmful microorganisms. The first segment 34 and the second segment 35 can be adjacent to one another, as depicted in FIG. 3, or can have a space 36 between each other, as shown in FIG. 4. And, also, preferably, the first segment 34 is installed nearer to the patient than is the second segment 35.

I claim:

1. A resuscitator, which comprises:
   a collapsible bag having an inlet for connection to a source of air or oxygen, a major outlet, and a minor outlet;
   a hollow three-armed connector having a first arm attached to the major outlet and communicating with an interior of said collapsible bag, a second arm available for connection to a nebulizer or aerosolizer, and a third arm;
   a flexible tube having a first end attached to the minor outlet of said collapsible bag and a second end available to connect to a nebulizer or aerosolizer;
   a housing having a first end attached to and communicating with the third arm of said hollow three-armed connector and containing a one-way valve to permit air, oxygen, and medication to flow from said hollow three-armed connector but precluding the transmission of liquids or gases toward said hollow three-armed connector, said housing also having a second end, and said housing containing, between the one-way valve and the second end of said housing, an exhaust aperture;
   a tube having a first aperture attached to and communicating with the second end of said housing, a second aperture, and a third aperture available for connection to a mask or an endotracheal tube.

2. The resuscitator as recited in claim 1, further comprising:
   a carbon dioxide detector inserted into the exhaust aperture.

3. The resuscitator as recited in claim 2, wherein:
   said carbon dioxide detector contains a detector filter.

4. The resuscitator as recited in claim 3, wherein:
   the detector filter comprises a first segment that is hydrophobic and a second segment that is hydrophilic.

5. The resuscitator as recited in claim 4, wherein:
   the first segment of the detector filter is installed nearer to the patient than is the second segment of the detector filter.

6. The resuscitator as recited in claim 1, further comprising:
   a filter covering said exhaust aperture.

7. The resuscitator as recited in claim 6, further comprising:
   a carbon dioxide detector inserted into the exhaust aperture.

8. The resuscitator as recited in claim 6, wherein:
   the filter comprises a first segment that is hydrophobic and a second segment that is hydrophilic.

9. The resuscitator as recited in claim 8, further comprising:
   a carbon dioxide detector inserted into the exhaust aperture.

10. The resuscitator as recited in claim 8, wherein:
    the first segment of the filter is installed nearer to the patient than is the second segment of the filter.

11. The resuscitator as recited in claim 10, further comprising:
    a carbon dioxide detector inserted into the exhaust aperture.

* * * * *